United States Patent [19]

Haas

[11] Patent Number: 4,695,630
[45] Date of Patent: Sep. 22, 1987

[54] CYCLOACETALS

[75] Inventor: Peter Haas, Haan, Fed. Rep. of Germany

[73] Assignee: Bayer Aktiengesellschaft, Leverkusen, Fed. Rep. of Germany

[21] Appl. No.: 821,569

[22] Filed: Jan. 22, 1986

[30] Foreign Application Priority Data

Feb. 9, 1985 [DE] Fed. Rep. of Germany ....... 3504480

[51] Int. Cl.⁴ .......................................... C07D 498/14
[52] U.S. Cl. ........................................ 544/75; 544/74
[58] Field of Search ...................................... 544/74, 75

[56] References Cited

FOREIGN PATENT DOCUMENTS 3331436  3/1985  Fed. Rep. of Germany .

OTHER PUBLICATIONS

Le Rouzic et al, Chemical Abstracts, vol. 103 (1985), 123419w.
Le Rouzic et al, Chemical Abstracts, vol. 104 (1985), 68815r.
Le Rouzic et al, Tetrahedron Letters, vol. 26, No. 15 (1985), pp. 1853–1856.

Primary Examiner—Richard L. Raymond
Attorney, Agent, or Firm—Sprung Horn Kramer & Woods

[57] ABSTRACT

New polycyclic acetals of the formula

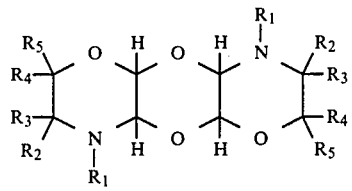

in which $R_1$ represents an optionally substituted alkyl, cycloalkyl, aralkyl, aryl or heteroaryl radical and $R_2$, $R_3$, $R_4$ and $R_5$ independently of one another denote hydrogen or an optionally substituted alkyl, cycloalkyl, aralkyl or aryl radical, or $R_3$ and $R_4$ together form an optionally substituted $C_2$–$C_6$-alkylene radical or $R_2$, $R_3$, $R_4$ and $R_5$ together form a fused, optionally substituted 1,2-phenylene radical, a process for their preparation and their use for the preparation of azalactones.

19 Claims, No Drawings

CYCLOACETALS

Cycloacetals are known; thus, for example, bicyclic acetals of glyoxal are described in Chem. Ber. 1954, page 1343 and Tetrahedron. volume 27, page 5579. They are obtained by reacting glyoxal with glycols, for example ethylene glycol.

The invention, on the other hand, relates to a completely novel type of cycloacetal, namely polycyclic acetals (4H,9H-octahydro-1,4-dioxano[2.3-b:5.6-b']bis[1,4]oxazines) of the formula

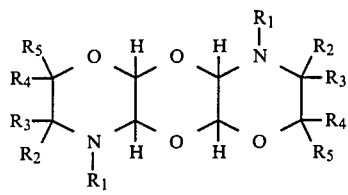

in which
- $R_1$ represents an optionally substituted alkyl, cycloalkyl, aralkyl, aryl or heteroaryl radical, preferably an optionally substituted $C_1$–$C_{12}$-alkyl, cyclopentyl, cyclohexyl, phenyl-$C_1$–$C_4$-alkyl or phenyl radical, and
- $R_2$, $R_3$, $R_4$ and $R_5$ independently of one another denote hydrogen, an optionally substituted alkyl, cycloalkyl, aralkyl, aryl or heteroaryl radical, preferably hydrogen, a $C_1$–$C_{12}$-alkyl radical or an optionally substituted cyclo-pentyl, cyclohexyl, phenyl-$C_1$–$C_4$-alkyl or phenyl radical; or $R_3$ and $R_4$ together form an optionally substituted $C_2$–$C_6$-alkylene radical, preferably a $C_3$–$C_4$-alkylene radical, or $R_2$, $R_3$, $R_4$ and $R_5$ together form a fused, optionally substituted 1,2-phenylene radical.

The following may be mentioned for $R_1$, $R_2$, $R_3$, $R_4$ and $R_5$:

as optionally substituted alkyl radicals: $C_1$–$C_{12}$-alkyl radicals, such as the methyl, ethyl, propyl, sec.-butyl, tert.-butyl, n-pentyl, n-hexyl or 2-ethylhexyl radical, and alkyl radicals which are substituted by halogen atoms, for example by fluorine and chlorine atoms, such as the trichloromethyl, fluoromethyl, difluoromethyl and trifluoromethyl radical; and also alkyl radicals which are substituted by heterocyclic groups, for example by the furyl, imidazolyl or triazolyl radical, such as the furfuryl, 2-(imidazol-2-yl)-ethyl and 2-(triazol-2-yl)-ethyl radical; and also alkyl radicals which are substituted by alkoxy or alkylmercapto groups, as optionally substituted cycloalkyl radicals: $C_5$–$C_7$-cycloalkyl radicals, such as the cyclopentyl radical and the cyclohexyl radical, and the cyclopentyl or cyclohexyl radicals which are substituted by $C_1$–$C_4$-alkyl groups and/or halogen atoms, for example chlorine or fluorine, such as the methylcyclohexyl, dimethylcyclohexyl or tert.-butylcyclohexyl radical, and halogenated, preferably chlorinated and/or fluorinated $C_5$–$C_7$-cycloalkyl radicals, such as the chlorocyclohexyl radical, the dichlorocyclohexyl radical and the trichloromethylcyclohexyl radical;

as optionally substituted aralkyl radicals: phenyl-$C_1$–$C_4$-alkyl radicals, such as the benzyl, α-methylbenzyl, 2-, 3- or 4-methylbenzyl, chlorobenzyl, dichlorobenzyl, trifluoromethylbenzyl and β-phenylethyl radical;

as optionally substituted aryl radicals: above all mononuclear aromatic aryl radicals, such as the phenyl, 4-chlorophenyl, 4-cyanophenyl, 4-fluorophenyl, tolyl and xylyl radical; and as optionally substituted heteroaryl radicals: the benzimidazole, benzotriazole, benzothiazole, phenothiazine, indole, carbazole, benzofuran and quinoline radical.

The following may be mentioned as examples of optionally substituted $C_2$–$C_6$-alkylene radicals which can be formed by $R_3$ and $R_4$ together: in particular $C_3$–$C_4$-alkylene radicals, such as the 1,3-propylene and 1,4-butylene radical; suitable substituents in these alkylene radicals are, above all, lower alkyl groups, such as the methyl group and the ethyl group.

Suitable substitutents for the fused 1,2-phenylene radical which can be formed by $R_2$, $R_3$, $R_4$ and $R_5$ together are, above all, lower alkyl groups, such as the methyl group or the tert.-butyl group, halogen atoms, such as chlorine or fluorine, and also the cyano group and nitro group.

The following may be mentioned as examples of representatives of the tricyclic acetals according to the invention of the formula (I):

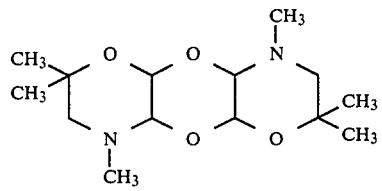

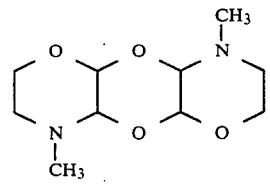

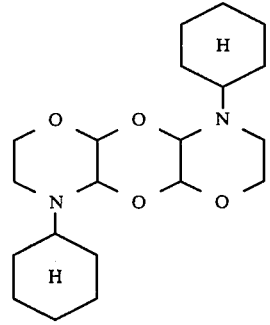

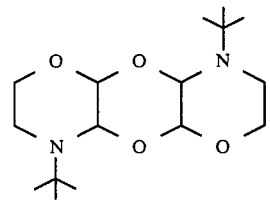

-continued
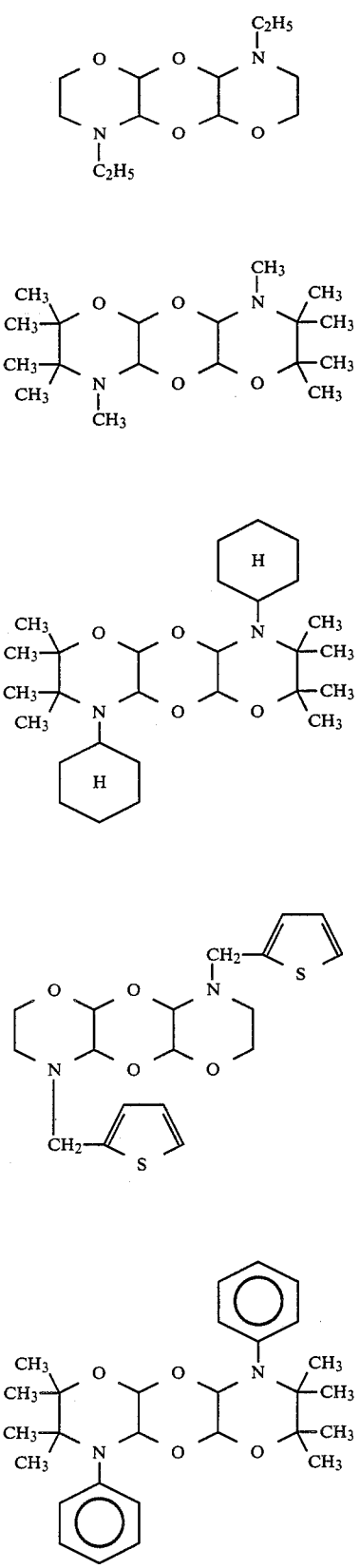
-continued
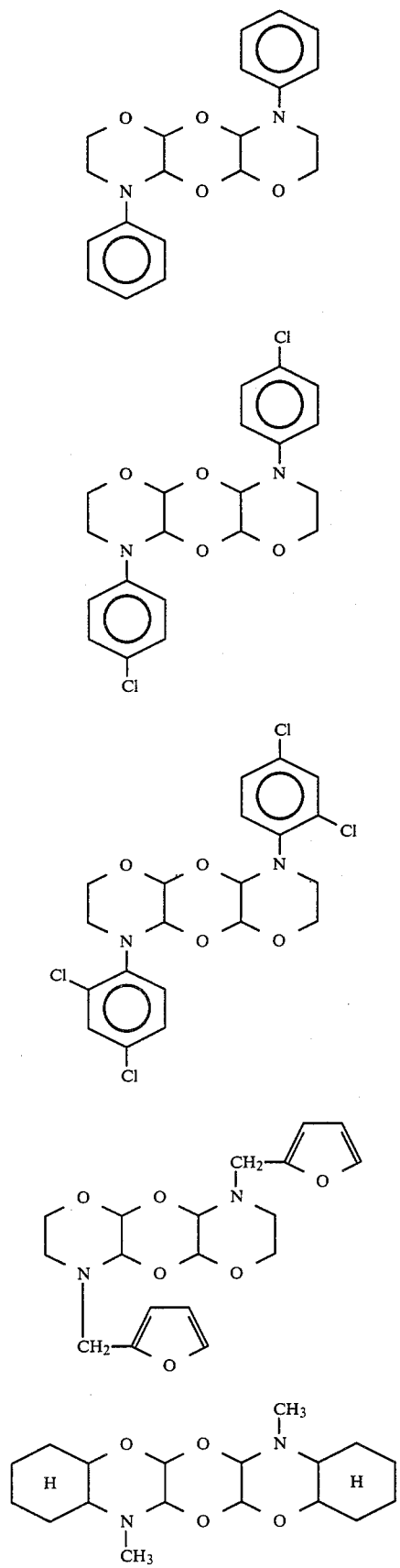

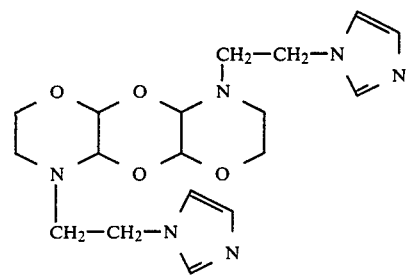
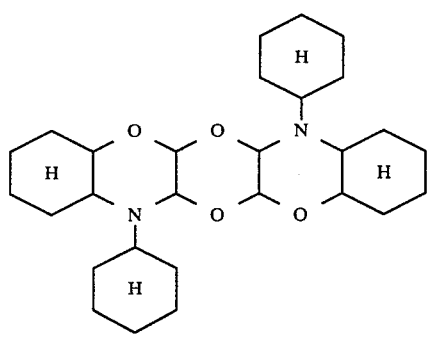
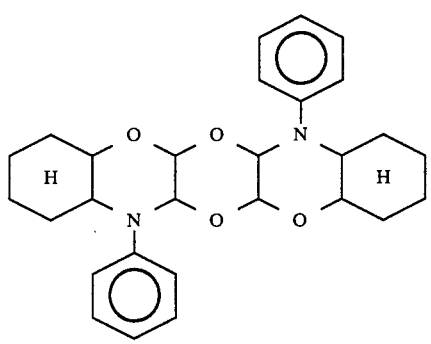
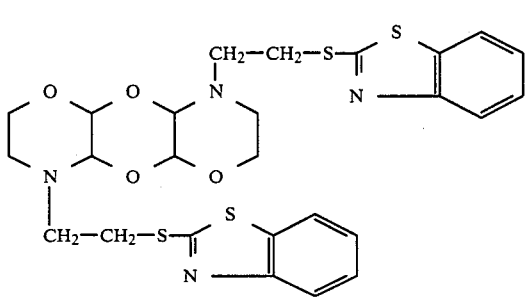
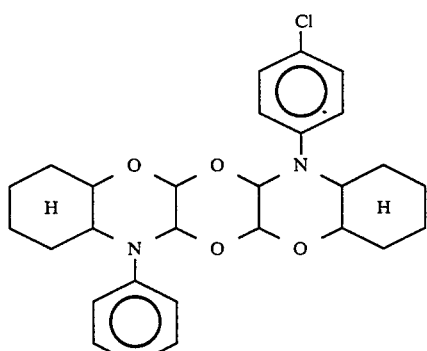
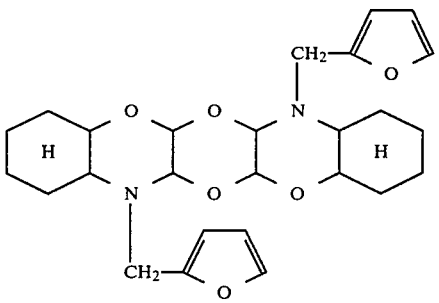
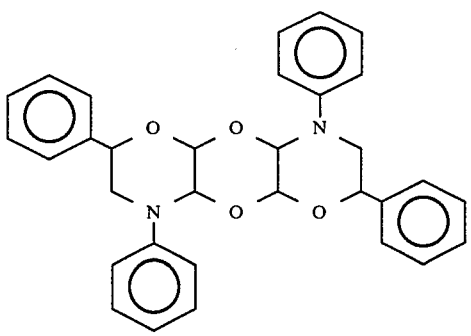
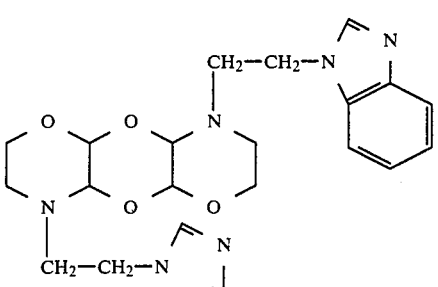
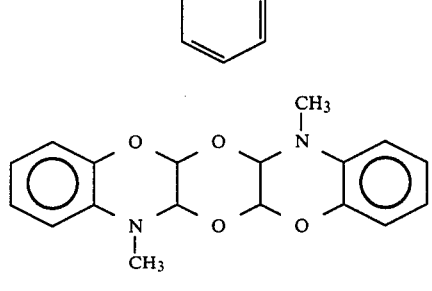
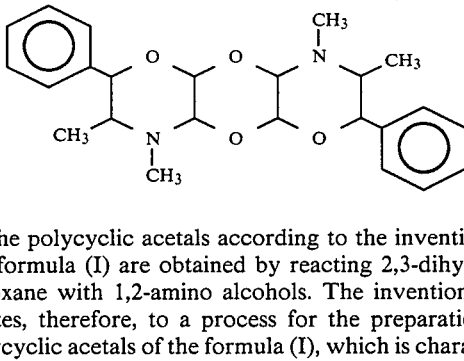
The polycyclic acetals according to the invention of the formula (I) are obtained by reacting 2,3-dihydroxydioxane with 1,2-amino alcohols. The invention also relates, therefore, to a process for the preparation of polycyclic acetals of the formula (I), which is characterised in that 2,3-dihydroxydioxane is reacted, preferably in an inert polar solvent, with 1,2-amino alcohols of the formula

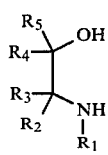 (II)

in which
R₁, R₂, R₃, R₄ and R₅ have the meaning indicated under formula (I).

The reaction, according to the invention, of the 2,3-dihydroxydioxane with the 1,2-amino alcohols can be described by means of the general equation:

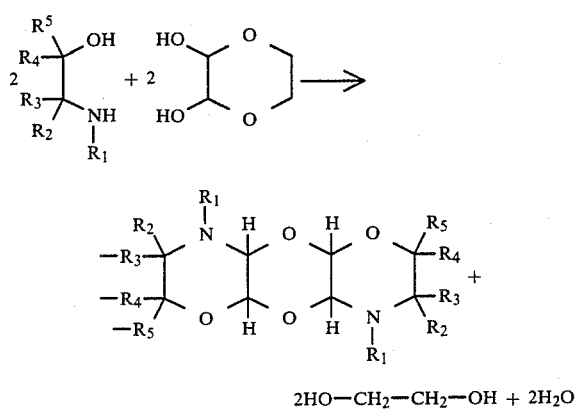

2HO—CH₂—CH₂—OH + 2H₂O

The following may be mentioned as examples of representatives of the 1,2-amino alcohols of the formula (II) which can be used in accordance with the invention: 2-N-methylaminoethan-1-ol, 2-N-cyclohexylaminoethan-1-ol, 2-N-tert.-butylaminoethan-1-ol, 2-N-ethylaminoethan-1-ol, 2-N-phenylaminoethan-1-ol, 2-(N-4-chlorophenyl)-aminoethan-1-ol, 2-(N-furfuryl-)aminoethan-1-ol, 2-N-methylaminocyclohexan-1-ol, 2-N-cyclohexylaminocyclohexan-1-ol, 2-N-phenylaminocyclohexan-1-ol, 2-N-chlorophenylaminocyclohexan-1-ol, 2-N-furfurylaminocyclohexan-1-ol, 2-N-methylaminocyclopentan-1-ol, 2-N-cyclohexylaminocyclopentan-1-ol, 2-N-phenylaminocyclopentan-1-ol, 2-N-chlorophenylaminocyclopentan-1-ol, 2-N-furfurylaminocyclopentan-1-ol, 2-N-cyclopentylaminocyclopentan-1-ol, 2-N-methylaminophenol, 2-N-cyclohexylaminophenol and 2-N-phenylaminophenol.

The reaction of the 2,3-dihydroxydioxane with the 1,2-amino alcohols is carried out at temperatures from 30° to 150° C., preferably 60° to 130° C. 2,3-dihydroxydioxane and 1,2-amino alcohols are preferably employed in equimolar amounts.

Water, dimethylformamide, dimethylacetamide, dioxane or dimethyl sulphoxide are preferably used as polar solvents which are inert under the reaction conditions.

It is preferable to carry out the reaction in such a way that the 2,3-dihydroxydioxane is dissolved in the intended solvent, for example water or dimethylformamide, and the 1,2-amino alcohol is added to this solution. If appropriate, the reaction mixture is then also warmed for a short while in order to complete the reaction. On cooling, the polycyclic cycloacetals of the formula (I) separate out, in most cases in the form of a crystalline precipitate. They are separated from the liquid phase in a customary manner, for example by filtering or centrifuging.

The polycyclic acetals according to the invention of the formula (I) open up a new and particularly simple route for the preparation of azalactones of the formula (III)

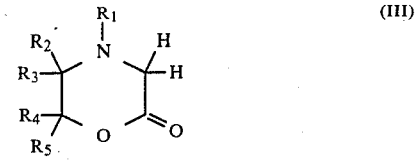 (III)

in which
R₁, R₂, R₃, R₄ and R₅ have the meaning indicated under formula (I).

It has been found that the polycyclic acetals, according to the invention, of the formula (I) are cleaved into the azalactones of the formula (III) in high yields, when heated above their melting point. The thermolysis of the cyclic acetals of the formula (I) can be illustrated by means of the following equation

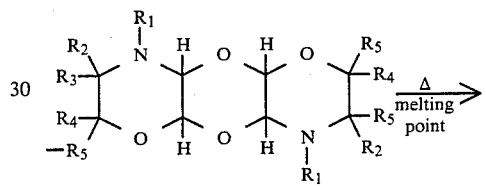

The thermolysis can be carried out either under normal pressure or under reduced pressure.

Some of the azalactones of the formula (III) are known; they are important starting compounds for the preparation of physiologically active dihydroxylated diphenylalkylamines (see Arch. Pharm. 316/83, page 339 et seq.).

These azalactones have hitherto been obtained by reacting sarcosine with epoxides. Although this process of preparation takes place with quite good yields, it has, however, the disadvantage that it is not universally applicable, that is to say applicable to the preparation of any desired substituted azalactones, because the epoxides required for the preparation of azalactones substituted by hetero-atoms, such as nitrogen and/or sulphur, are not accessible.

In contrast with the synthesis of the azalactones from sarcosine and epoxides, the thermolysis of the polycyclic acetals according to the invention of the formula (I) constitutes a simple and extensively applicable process for the preparation of any desired substituted azalactones from precursors which are readily accessible.

The invention also relates, therefore, to the use of the polycyclic lactones, according to the invention, of the formula (I) as intermediate products for the preparation of azalactones of the formula (III). The following may be mentioned as examples of representatives of the azalactones of the formula (III) which can be prepared in accordance with the invention:
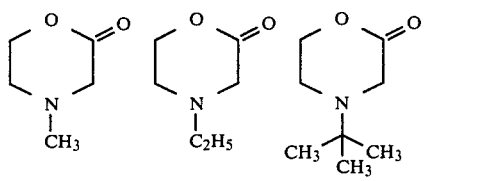
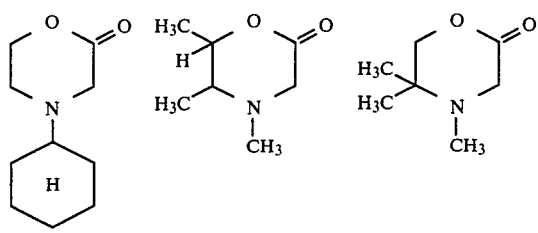
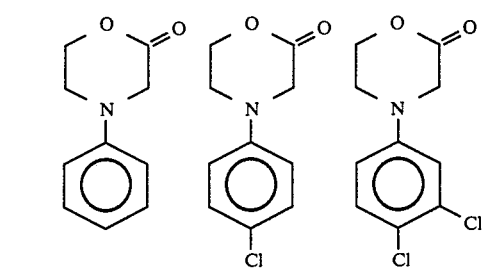
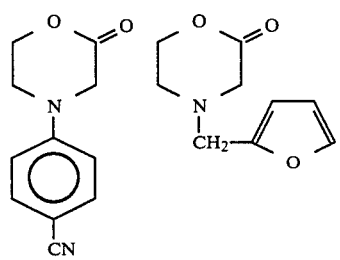
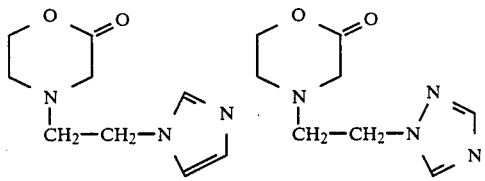
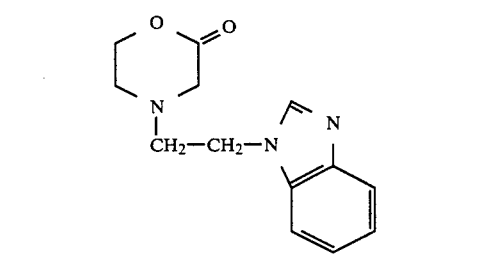
-continued
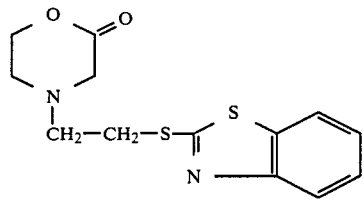
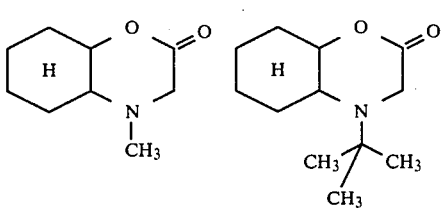
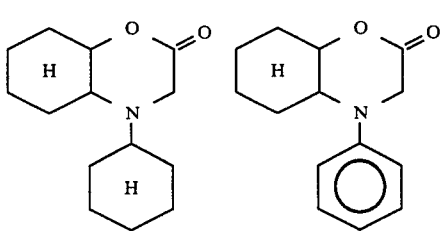
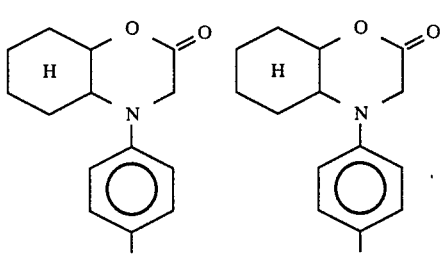
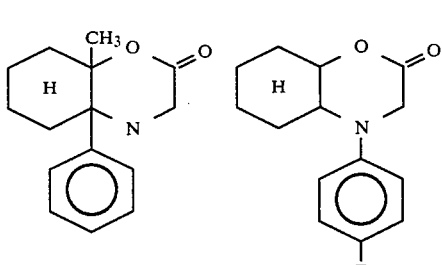
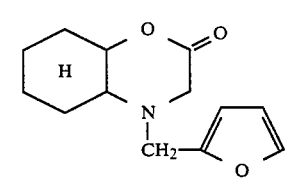
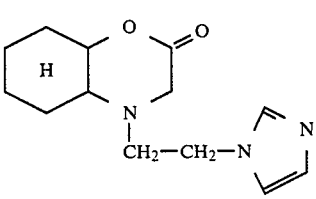

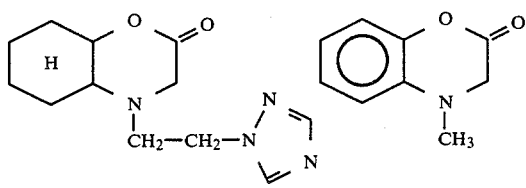

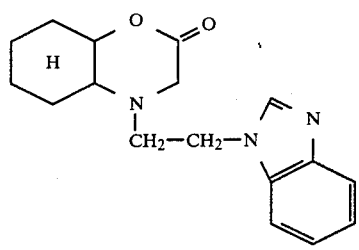

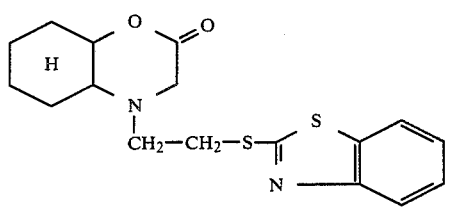

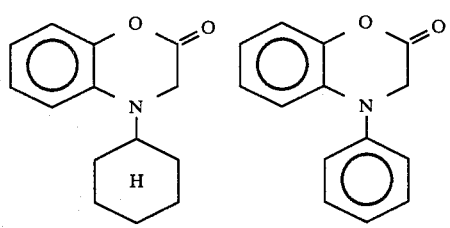

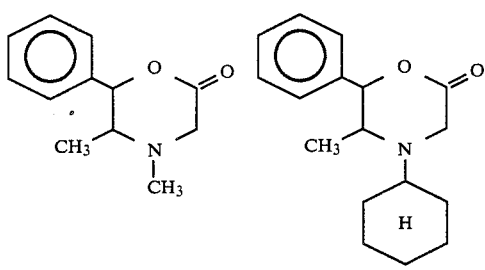

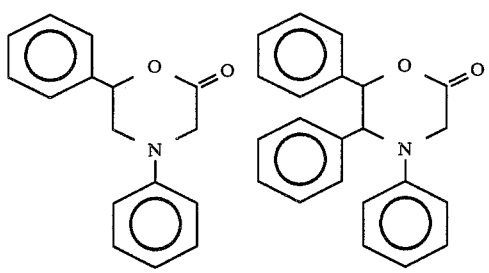

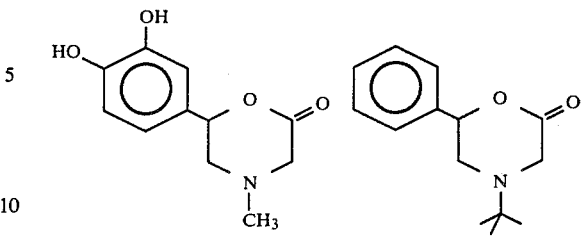

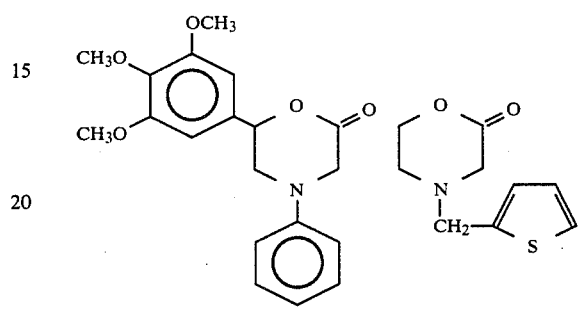

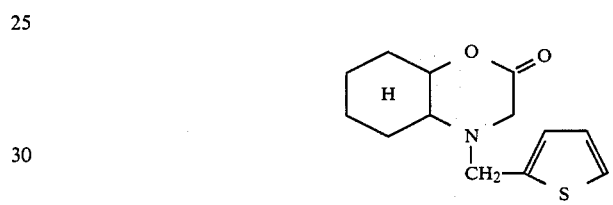

The reaction, according to the invention, of the 2,3-dihydroxydioxanes with the 1,2-amino alcohols is independent of the nature of the substituents $R_1$, $R_2$, $R_3$, $R_4$ and $R_5$ of the amino alcohol. In principle, any desired substituted amino alcohol in which amino and hydroxyl groups are located in the 1,2-position relative to one another can be employed. This explained the very wide applicability of the process according to the invention (a) for the preparation of the polycyclic cycloacetals of the formula (I) and (b) for the preparation of the azalactones of the formula (III).

By means of the reaction, according to the invention, of the 2,3-dihydroxydioxane with the 1,2-aminoalcohols of the formula (II) to give the polycyclic acetals of the formula (I) and the thermolysis of these cyclic acetals of the formula (I) to give azalactones of the formula (III), not only are known azalactones rendered accessible by a simpler method, but the preparation of a large number of azalactones also becomes possible, as the result of a simple reaction, which can also be carried out on a technical scale.

EXAMPLE 1

(a)

Preparation of 4,9-dimethyl-4H,9H-octahydro-1,4-dioxano[2.3-b;5.6-b']bis[1,4]oxazine (1a)

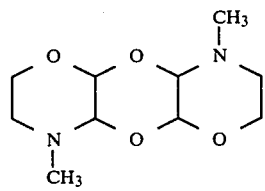

150 g of 2-N-methylaminoethan-1-ol are added dropwise at room temperature to a solution of 240 g (2 mol) of 2,3-dihydroxydioxane in 300 ml of dimethylformamide; in the course of this the temperature of the reaction mixture rises to 30° C. The reaction mixture is then stirred for 2 hours. The crystalline precipitate is then filtered off with suction and boiled up in ethyl acetate. This gives 225 g (=98% of theory) of the compound (1a) in the form of colourless crystals of melting point 176° C. (decomposition). Empirical formula $C_{10}H_{18}N_2O_4$, molecular weight: 230.

Analytical data: calculated C: 52.2%, H: 7.8%, N: 12.1%; found C: 52.3%, H: 7.7%, N: 12.1%.

(b)

Thermolysis to give 4-N-methylmorpholin-2-one 50 g of the compound (1a) are heated at 175° C. in a closed flask equipped with a stirrer until the entire product has become liquid. The liquid product is then cooled and distilled in vacuo. This gives 48 g (=96% of theory) of 4-N-methylmorpholin-2-one in the form of a colourless liquid (boiling point 56°-58° C. at 0.09 mbar). Empirical formula $C_5H_9NO_2$, molecular weight: 115.

Analytical data: calculated C: 52.2%, H: 7.8%, N: 12.1%; found C: 52.2%, H: 7.8%, N: 12.1%.

EXAMPLE 2

(a)

Preparation of 4,9-dicyclohexyl-4H,9H-octahydro-1,4-dioxano[2.3-b:5.6-b']bis[1,4]oxazine (2a)

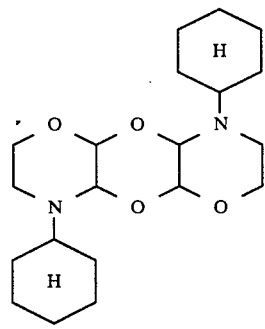

A solution of 57.2 g (0.4 mol) of 2-N-cyclohexylaminoethan-1-ol in 20 ml of dimethylformamide is added, at room temperature and with stirring, to a solution of 48 g (0.4 mol) of 2,3-dihydroxydioxane in 60 ml of dimethylformamide. A clear solution is formed, from which a crystalline precipitate separates out after stirring for about one hour. The precipitate is filtered off with suction and boiled up in 100 ml of ethyl acetate. This gives 66 g (=90% of theory) of the compound (2a) in the form of colourless crystals of melting point 174°-177° C. (decomposition). Empirical formula $C_{20}H_{34}N_2O_4$, molecular weight: 366.

Analytical data: calculated C: 65.5%, H: 9.3%, N: 7.6%; found C: 64.8%, H: 9.0%, N: 7.5%.

(b)

Thermolysis to give 4-N-cyclohexylmorpholin-2-one 36.6 g of the compound (2a) are heated at 190° C. in a closed flask equipped with a stirrer until the entire mass has become liquid. The liquid is cooled and distilled in vacuo. This gives 33 g (=90% of theory) of 4-N-cyclohexylmorpholin-2-one in the form of a colourless liquid (boiling point: 116° C. at 0.1 mbar). Empirical formula $C_{10}H_{17}NO_2$, molecular weight: 183.

Analytical data: calculated C: 65.5%, H: 9.3%, N: 7.6%; found C: 65.0%, H: 9.3%, N: 7.8%.

EXAMPLE 3

(a)

Preparation of 4,9-diphenyl-4H,9H-octahydro-1,4-dioxano[2.3-b:5.6-b']bis[1,4]oxazine (3a)

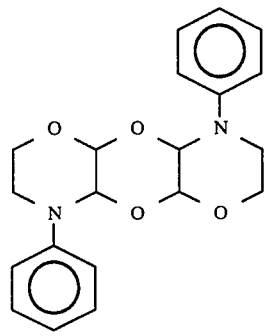

54.8 g (0.4 mol) of N-2-hydroxyethylaniline are added dropwise, at room temperature and with stirring to a solution of 48 g (0.4 mol) of 2,3-dihydroxydioxane in 50 ml of dimethylformamide. The solution is heated at 80° C. for 1 hour. After cooling, the precipitate is filtered off with suction and boiled up with dioxane. This gives 60 g (=84% of theory) of the compound (3a) in the form of colourless crystals of melting point 225°-258° C. (decomposition). Empirical formula $C_{20}H_{22}N_2O_4$, molecular weight: 354.

Analytical data: calculated C: 67.7%, H: 6.2%, N: 7.9%; found C: 67.9%, H: 6.3%, N: 8.1%.

(b)

Thermolysis to give 4-N-phenylmorpholin-2-one (3b)

35.4 g (0.1 mol) of the compound (3a) are heated at 240° C. in a closed flask equipped with a stirrer until a clear liquid has been formed. The liquid is cooled and then distilled in vacuo. This gives 30 g (=84% of theory) of 4-N-methylmorpholin-2-one in the form of a clear liquid (boiling point: 146°-156° C. at 0.2 mbar), which rapidly crystallises in the form of colourless leaflets on cooling. Melting point: 71°-73° C. Empirical formula $C_{10}H_{11}NO_2$.

EXAMPLE 4

(a)

Preparation of
4,9-dimethyl-2,3,7,8-bistetramethylene-4H,9H-octahydro-1,4-dioxano[2.3-b:5.6-b']bis[1,4]oxazine (4a)

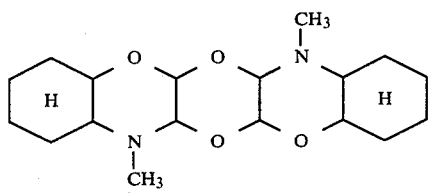

51.6 g (0.4 mol) of 2-N-methylaminocyclohexan-1-ol are added, at room temperature and with stirring, to a solution of 48 g (0.4 mol) of 2,3-dihydroxydioxane in 40 ml of dimethylformamide. The solution is heated at 80° C. for 5 hours. On cooling, a colourless precipitate crystallises from the solution. 59 g (=86% of theory) of the compound (4a) are obtained in the form of colourless crystals of melting point 242°–245° C. (decomposition). Empirical formula $C_{18}H_{30}N_2O_4$, molecular weight: 338.

Analytical data: calculated C: 63.7%, H: 8.8%, N: 8.3%; found C: 63.6%, H: 8.3%, N: 8.5%.

(b)

Thermolysis to give
4-N-methyl-5,6-tetramethylenemorpholin-2-one (4b)

33.8 g (0.1 mol) of the compound (4a) are heated at 250° C. until a clear liquid has been formed. The liquid is cooled and distilled in vacuo. This gives 28 g (=83% of theory) of 4-N-methyl-5,6-tetramethylenemorpholin-2-one in the form of a slightly viscous oil (boiling point: 99°–101° C. at 0.09 mbar). Empirical formula $C_9H_{15}NO_2$, molecular weight: 169.

Analytical data: calculated C: 63.7%, H: 8.8%, N: 8.3%; found C: 63.6%, H: 8.5%, N: 8.6%.

EXAMPLE 5

(a)

Preparation of
4,9-bisfurfuryl-2,3,7,8-bistetramethylene-4H,9H-octahydro-1,4-dioxano[2.3-b:5.6-b']bis[1,4]oxazine (5a)

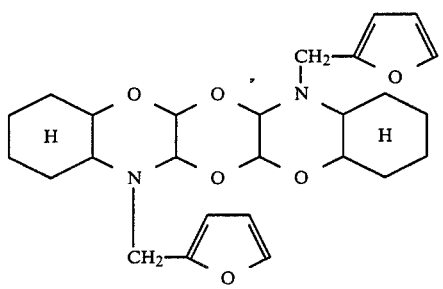

78 g (0.4 mol) of 2-N-furfurylaminocyclohexan-1-ol are added, at room temperature and with stirring, to a solution of 48 g (0.4 mol) of 2,3-dihydroxydioxane in 40 ml of dimethylformamide. The solution is heated at 80° C. for 2 hours. After cooling, the precipitate which has crystallised out is filtered off with soction and boiled up in ethyl acetate. This gives 80.6 g (=85% of theory) of the compound (5a) in the form of colourless crystals of melting point 221°–226° C. (decomposition), Empirical formula $C_{26}H_{34}N_2O_6$, molecular weight: 470.

Analytical data: calculated C: 66.3%, H: 7.2%, N: 5.9%; found C: 66.4%, H: 7.1%, N: 5.9%.

(b)

Thermolysis to give
4-N-furfuryl-5,6-tetramethylenemorpholin-2-one (5b)

47 g (0.1 mol) of the compound (5a) are heated at 230° C. until a clear liquid has been formed. The liquid is cooled and distilled in vacuo. This gives 39 g (=83% of theory) of 4-N-furfuryl-5,6-tetramethylenemorpholin-2-one in the form of a clear liquid (boiling point: 172°–177° C. at 0.14 mbar). Empirical formula $C_{13}H_{17}NO_3$, molecular weight: 235.

Analytical data: calculated C: 66.3%, H: 7.2%, N: 5.9%; found C: 66.3%, H: 7.2%, N: 5.8%.

EXAMPLE 6

(a)

Preparation of
2,7-diphenyl-3,4,8,9-tetramethyl-4H,9H-octahydro-1,4-dioxano[2.3-b:5.6-b']bis[1,4]oxazine (6a)

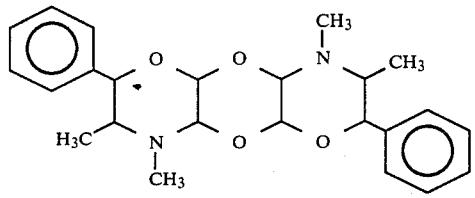

64 g (0.4 mol) of 1(-)-ephedrine are added, at room temperature and with stirring, to a solution of 48 g (0.4 mol) of 2,3-dihydroxydioxane in 50 ml of dimethylformamide. The solution is heated at 70° C. for 2 hours. The reaction mixture is then freed from all volatile compounds under a high vacuum. The distillation residue crystallises slowly. The crystalline product is dried on clay. 60 g (=73% of theory) of the compound (6a) are obtained in the form of a crystalline mass of melting point 175° C. (decomposition). Empirical formula $C_{24}H_{30}N_2O_4$, molecular weight: 410

Analytical data: calculated C: 70.2%, H: 7.3%, N: 6.8%; found C: 69.0%, H: 7.4%, N: 6.5%.

(b)

Thermolysis to give
4,5-dimethyl-6-phenylmorpholin-2-one (6b)

4.1 g (0.1 mol) of the compound (6a) are heated at 180° C. until a clear liquid has been formed. The liquid is cooled and distilled in vacuo. This gives 3.5 g (=85% of theory) of 4,5-dimethyl-6-phenylmorpholin-2-one in the form of a colourless liquid (boiling point: 128° to 134° C. at 0.02 mbar). Empirical formula $C_{12}H_{15}NO_2$.

Analytical data: calculated C: 70.2%, H: 7.3%, N: 6.8%; found C: 69.5%, H: 7.4%, N: 7.2%.

EXAMPLE 7

Preparation of 4,9-bis-tert.-butyl-4H,9H-octahydro-1,4-dioxano[2.3-b:5.6-b']bis[1,4]oxazine (7a)

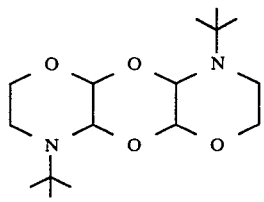

A solution of 23.4 g (0.2 mol) of 2-N-butylaminoethan-1-ol in 10 ml of dimethylformamide is added dropwise, at room temperature and with stirring to a solution of 24 g (0.2 mol) of 2,3-dihydroxydioxane in 30 ml of dimethylformamide. The solution is heated at 50° C. for 2 hours and is kept overnight. The precipitate is filtered off with suction and recrystallised from dimethylformamide. This gives 25.4 g (=80% of theory) of the compound (7a) of melting point 170°–173° C. (decomposition).

Empirical formula $C_{16}H_{30}N_2O_4$, molecular weight: 311.

Analytical data: calculated C: 61.1%, H: 9.6%, N: 8.9%; found C: 61.2%, H: 9.1%, N: 8.5%.

EXAMPLE 8

Preparation of 4,9-bis-(4-chlorophenyl)-4H,9H-octahydro-1,4-dioxano[2.3-b:5.6-b']bis[1,4]oxazine (8)

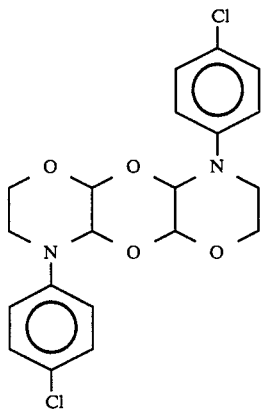

34.2 g (0.2 mol) of N-(4-chlorophenyl)-ethanolamine are added, at room temperature and with stirring, to a solution of 24 g (0.2 mol) of 2,3-dihydroxydioxane in 50 ml of dimethylformamide. The solution is heated at 70° for one hour and is then freed in vacuo from all volatile compounds. The residue is recrystallised from dimethylformamide. 28 g (=65% of theory) of the compound (8) of melting point 279°–282° C. (decomposition) are obtained. Empirical formula $C_{20}H_{20}Cl_2N_2O_4$, molecular weight: 423.

Analytical data: calculated C: 56.8%, H: 4.7%, N: 6.6%, Cl: 16.8%; found C: 57.0%, H: 4.8%, N: 6.5%, Cl: 16.8%.

EXAMPLE 9

Preparation of 4,9-bis-(4-chlorophenyl)-2,3,7,8-bis-tetramethylene-4H,9H-octahydro-1,4-dioxano[2.3-b:5.6-b']bis[1,4]oxazine (9)

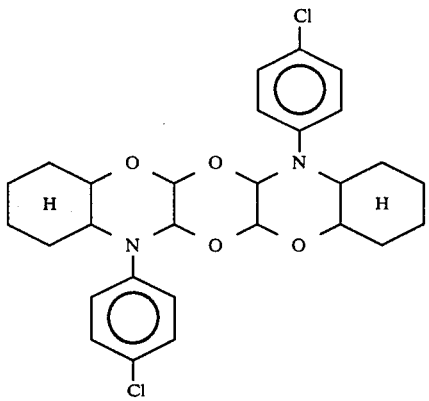

44.4 g (0.2 mol) of 2-N-(4-chlorophenyl)-aminohexan-1-ol are added with stirring to a solution of 24 g (0.2 mol) of 2,3-dihydroxydioxane in 50 ml of dimethylformamide. The solution is heated at 100° C. for 3 hours. After cooling, the precipitate is filtered off with suction. 25 g (=47% of theory) of the compound (9) are obtained in the form of colourless crystals of melting point 291°–293° C. Empirical formula $C_{28}H_{32}Cl_2N_2O_4$, molecular weight: 531.

Analytical data: calculated C: 63.3%, H: 6.0%, N: 5.2%, Cl: 13.4%; found C: 62.7%, H: 6.1%, N: 5.2%, Cl: 13.4%.

What is claimed is:
1. A polycyclic acetal of the formula

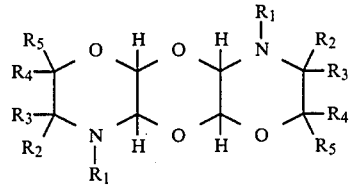

in which
R₁ is an unsubstituted alkyl or an alkyl substituted by a substituent selected from the group consisting of a halogen, a heterocyclic group, an alkoxy group and an alkylmercapto group, an unsubstituted cycloalkyl or a cycloalkyl substituted by a substituent selected from the group consisting of $C_1$-$C_4$ alkyl groups and halogen atoms, an unsubstituted aralkyl or an aralkyl substituted by a substituent selected from the group consisting of methyl, chloro, and trifluoromethyl, an unsubstituted aryl or aryl substituted by a substituent selected from the group consisting of cyano, fluoro, chloro and methyl or a heteroaryl radical and R₂, R₃, R₄ and R₅ independently of one another are hydrogen or an unsubstituted alkyl or an alkyl substituted by a substituent selected from the group consisting of a halogen, a heterocyclic group, an alkoxy group and an alkylmercapto group, an unsubstituted cycloalkyl or a cycloalkyl substituted by a substituent selected from the group consisting of $C_1$-$C_4$ alkyl groups and halogen atoms, an unsubstituted aralkyl or an aralkyl substituted by a substituent selected from the group consisting of methyl, chloro, and trifluoromethyl, an unsubstituted aryl radical or aryl radical substituted by a substituent selected from the group consisting of cyano, fluoro, chloro and methyl, or $R_3$ and $R_4$ together form an unsubstituted $C_2$–$C_6$-alkylene radical or a $C_2$–$C_6$-alkylene radical substituted by a lower alkyl group, $R_2$, $R_3$, $R_4$ and $R_5$ together form a fused, unsubstituted 1,2-phenylene radical or a 1,2-phenylene radical substituted by a substituent selected from the group consisting of a lower alkyl group, a halogen atom, a cyano group and a nitro group.

2. The polycyclic acetal of claim 1, wherein $R_1$ is an an unsubstituted $C_1$–$C_{12}$-alkyl or $C_1$–$C_{12}$ alkyl substituted by a substituent selected from the group consisting of a halogen, a heterocylic radical, an alkoxy group and an alkylmercapto group, unsubstituted cyclopentyl or cyclopentyl substituted by a substituent selected from the group consisting of $C_1$–$C_4$ alkyl groups and halogen atoms, unsubstituted cyclohexyl or cyclohexyl substituted by a substituent selected from the group consisting of $C_1$–$C_4$ alkyl groups and halogen atoms, unsubstituted phenyl-$C_1$–$C_4$-alkyl or phenyl-$C_1$–$C_4$-alkyl substituted by a substituent selected from the group consisting of methyl chloro and trifluoromethyl, unsubstituted phenyl or phenyl substituted by a substituent selected from the group consisting of cyano, fluoro, chloro and methyl and $R_2$, $R_3$, $R_4$, and $R_5$ independently of one another are hydrogen, a $C_1$–$C_{12}$-alkyl radical or unsubstituted cyclopentyl or cyclopentyl substituted by a substituent selected from the group consisting of $C_1$–$C_4$-alkyl and halogen, unsubstituted cyclohexyl or cyclohexyl substituted by a substituent selected from the group consisting of $C_1$–$C_4$-alkyl and halogen, unsubstituted phenyl-$C_1$–$C_4$-alkyl or phenyl-$C_1$–$C_4$-alkyl substituted by a substituent selected from the group consisting methyl, chloro and trifluoromethyl, or unsubstituted phenyl or phenyl substituted by a substituent, selected from the group consisting of cyano, fluoro, chloro and methyl, or $R_3$ and $R_4$ together form an unsubstituted $C_3$-$C_4$-alkylene radical or a $C_3$-$C_4$-alkylene radical substituted by a lower alkyl group or $R_2$, $R_3$, $R_4$, $R_5$ together form a fused, unsubstituted 1,2-phenylene radical or a 1,2-phenylene radical substituted by a substituent selected from the group consisting of a lower alkyl group, a halogen atom, a nitro group and a cyano group.

3. A process for the preparation of a polycyclic acetal of the formula

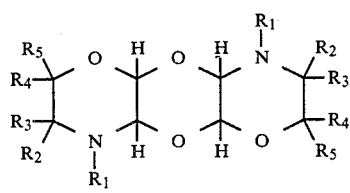

in which $R_1$ is as defined in claim 1, $R_2$, $R_3$, $R_4$ and $R_5$ are as defined in claim 1, comprising reacting a 2,3-dihydroxydioxane with an 1,2-amino alcohol of the formula

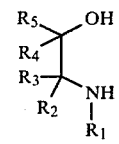

in which $R_1$, $R_2$, $R_3$, $R_4$ and $R_5$ have the meanings indicated above.

4. A polycyclic acetal according to claim 1, wherein said halogen is selected from the group consisting of fluorine and chlorine.

5. A polycyclic acetal according to claim 1, wherein said heterocyclic group is selected from the group consisting of furyl, imidazolyl and triazolyl.

6. A polycyclic acetal according to claim 1, wherein the said alkyl group substituted by a heterocyclic group is selected from the group consisting of furfuryl, 2-(imidazol-2-yl)-ethyl and 2-(triazol-2-yl)-ethyl.

7. A polycyclic acetal according to claim 1, wherein said cycloalkyl is substituted by a substituent selected from the group consisting of chlorine, fluorine, methyl, dimethyl and tert.-butyl.

8. A polycyclic acetal according to claim 1, wherein the aralkyl radical is a phenyl-$C_1$–$C_4$-alkyl radical.

9. A polycyclic acetal according to claim 8, wherein the aralkyl radical is benzyl.

10. A polycyclic acetal according to claim 1, wherein the aralkyl radical is selected from the froup consisting of alpha-methylbenzyl, 2-methylbenzyl, 3-methylbenzyl, 4-methylbenzyl, chlorobenzyl, dichlorobenzyl, trifluoromethylbenzyl and beta-phenylethyl.

11. A polycyclic acetal according to claim 1, wherein the aryl radical is selected from the group consisting of phenyl, 4-chlorophenyl, 4-cyanophenyl, 4-fluorophenyl, tolyl and xylyl.

12. A polycyclic acetal according to claim 1, wherein the heteroaryl radical is selected from the group consisting of benzimidazole, benzotriazole, benzothiazole, phenothiazine, indole, carbazole, benzofuran and quinoline.

13. A polycyclic acetal according to claim 1, wherein the $C_2$–$C_6$-alkylene radical is selected from the group consisting of 1,3-propylene and 1,4-butylene.

14. A polycyclic acetal according to claim 1, wherein the lower alkyl group substituent for the $C_2$–$C_6$-alkylene radical is selected from the group consisting of methyl and ethyl.

15. A polycyclic acetal according to claim 1, wherein for the substituents for the fused 1,2-phenylene radical the lower alkyl group is selected from the group consisting of methyl and tert.-butyl and wherein the halogen is selected from the group consisting of chlorine and fluorine.

16. A polycyclic acetal of claim 1, wherein $R_1$ is $C_1$–$C_{12}$-alkyl or $C_1$–$C_{12}$-alkyl substituted by a substituent selected from the group consisting of a halogen, a heterocyclic group, an alkoxy group and an alkylmercapto group; cyclopentyl or cyclopentyl substituted by a substituent selected from the group consisting of $C_1$–$C_4$-alkyl and halogen; cyclohexyl or cyclohexyl substituted by a substituent selected from the group consisting of $C_1$–$C_4$-alkyl and halogen; phenyl-$C_1$–$C_4$-alkyl; phenyl or phenyl substituted by a substituent selected from the group consisting of fluoro, chloro, cyano and methyl, $R_2$, $R_3$, $R_4$ and $R_5$ independently of one another are hydrogen, $C_1$–$C_{12}$-alkyl, cyclopentyl; cyclopentyl substituted by a substituent selected from the group consisting of $C_1$–$C_4$-alkyl and halogen; cyclohexyl or cyclohexyl substituted by a substituent selected from the group consisting of $C_1$–$C_4$-alkyl and halogen; phenyl-$C_1$–$C_4$-alkyl; or phenyl or $R_3$ and $R_4$ together form an $C_3$–$C_4$-alkylene radical or an $C_3$–$C_4$-alkylene radical substituted by lower alkyl; or $R_2$, $R_3$, $R_4$ and $R_5$ form a fused 1,2-phenylene radical or a fused 1,2-phenylene radical substituted by a substituent selected from the group consisting of halogen and $C_1$–$C_4$-alkyl.

17. A polycyclic acetal of claim 1, wherein $R_1$ is $C_1$–$C_4$-alkyl or $C_1$–$C_4$-alkyl substituted by a substituent selected from the group consisting of fluoro, chloro and a heterocyclic group; cyclopentyl; cyclohexyl; phenyl-$C_1$–$C_4$-alkyl; phenyl or phenyl substituted by a substituent selected from the group consisting of fluoro, chloro, cyano and methyl; $R_2$, $R_3$, $R_4$ and $R_5$ independently of one another are hydrogen; $C_1$–$C_4$-alkyl; or phenyl or $R_3$ and $R_4$ together form an $C_3$–$C_4$ alkylene radical; or $R_2$, $R_3$, $R_4$ and $R_5$ form a fused 1,2-phenylene radical.

18. A polycyclic acetal of claim 1, wherein $R_1$ is $C_1$–$C_4$-alkyl or $C_1$–$C_4$-alkyl substituted by a substituent selected from the group consisting of fluoro, chloro, furyl, an imidazolyl or a triazolyl-radical; cyclopentyl, cyclohexyl, benzyl, phenyl or phenyl substituted by a substituent selected from the group consisting of fluoro, chloro, cyano and methyl;

$R_2$, $R_3$, $R_4$ and $R_5$ independently of one another are hydrogen, methyl, or phenyl, or $R_3$ and $R_4$ together form an $C_4$-alkylene radical; or $R_2$, $R_3$, $R_4$ and $R_5$ form a fused phenylene radical.

19. A process according to claim 3, further comprising conducting the reaction in the presence of an inert polar solvent.

* * * * *